United States Patent [19]
Epstein

[11] 3,993,948
[45] Nov. 23, 1976

[54] PARTICLE ANALYZER HAVING SCANNING APPARATUS SERIES COUPLED BETWEEN A D.C. POWER SOURCE AND THE PARALLEL CONNECTION OF A D.C. SHORT-CIRCUITING DEVICE AND A VOLTAGE SENSITIVE SIGNAL DETECTOR

[75] Inventor: Sheldon L. Epstein, Wilmette, Ill.
[73] Assignee: Coulter Electronics, Inc., Hialeah, Fla.
[22] Filed: Dec. 8, 1971
[21] Appl. No.: 206,045

Related U.S. Application Data

[63] Continuation of Ser. No. 882,366, Dec. 15, 1969, abandoned, which is a continuation of Ser. No. 475,944, July 30, 1965, abandoned.

[52] U.S. Cl. .......................... 324/71 CP; 324/30 R
[51] Int. Cl.² .................. G01N 27/00; G01N 27/42
[58] Field of Search .............. 324/71 CP, 30 R, 62, 324/65

[56] References Cited
UNITED STATES PATENTS

| | | | |
|---|---|---|---|
| 2,656,508 | 10/1953 | Coulter | 324/71 CP |
| 2,683,986 | 7/1954 | Bartlett et al. | 324/71 CP |
| 2,702,471 | 2/1955 | Vonnegut | 324/30 R X |

OTHER PUBLICATIONS

Belt W. and Kaizer C., D.C. Power Supplies In System Designer's Handbook–Electrochemical De ign July 1964, pp. 181–193.

*Primary Examiner*—John K. Corbin
*Assistant Examiner*—Rolf Hille
*Attorney, Agent, or Firm*—Silverman & Cass, Ltd.

[57] ABSTRACT

A particle analyzer having a low impedance low voltage d.c. source series connected to a scanner and the parallel combination of a d.c. short-circuiting device and a high input impedance, voltage sensitive signal detector. A d.c. current flowing in the scanning ambit is modulated by the passage of particles therein. The detection of particles is unaffected by long term changes in the conductivity of the fluid medium which carries the particles within the scanning ambit, since the d.c. current then flowing in the scanning ambit is caused to be deliberately variable and inversely proportional to the resistivity of the fluid medium.

20 Claims, 7 Drawing Figures

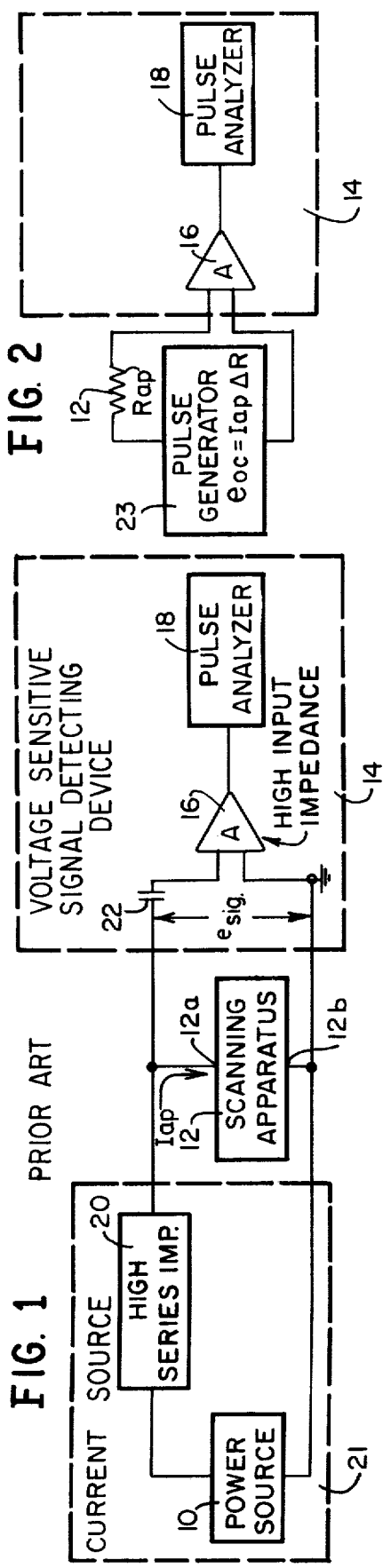
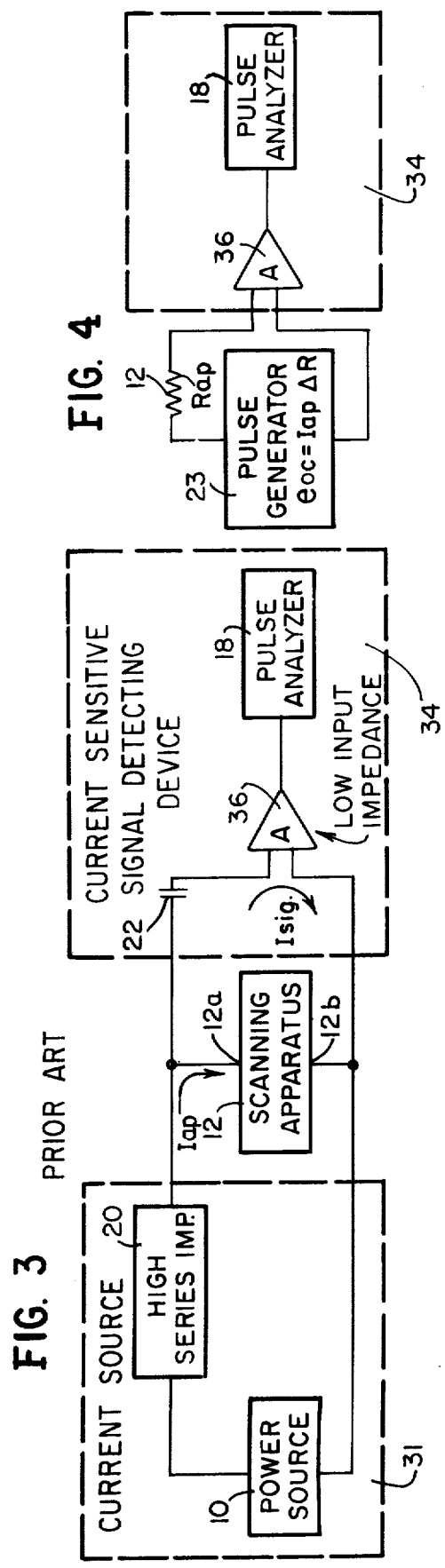

3,993,948

PARTICLE ANALYZER HAVING SCANNING APPARATUS SERIES COUPLED BETWEEN A D.C. POWER SOURCE AND THE PARALLEL CONNECTION OF A D.C. SHORT-CIRCUITING DEVICE AND A VOLTAGE SENSITIVE SIGNAL DETECTOR

CROSS REFERENCE TO RELATED APPLICATIONS

This application is a Continuation of my co-pending application "A PARTICLE ANALYZER HAVING SCANNING APPARATUS SERIES COUPLED BETWEEN A VOLTAGE SOURCE AND THE PARALLEL CONNECTION OF A CURRENT TO VOLTAGE TRANSFORMATION CIRCUIT AND A VOLTAGE SENSITIVE SIGNAL DETECTOR", Ser. No. 882,366, filed on Dec. 15, 1969 now abandoned; which is a Continuation application of my, now abandoned, application Ser. No. 475,944, filed on July 30, 1965, entitled "PARTICLE STUDY APPARATUS".

BACKGROUND OF THE INVENTION

This invention relates generally to the art of studying particles and more particularly is concerned with a structure for use in analyzing particles which are suspended in a liquid medium. Specifically, this invention is directed to particle analyzers constructed for operating in mode independent of changes in the resistivity of the liquid medium in which the particles are suspended.

DESCRIPTION OF THE PRIOR ART

The basic structure of an apparatus of the general type here involved is described and claimed in U.S. Pat. No. 2,656,508. The invention herein is an improvement of the basic structure in that the improved structure is not sensitive to changes in aperture liquid conductivity, to electro-chemically generated voltages and to other variables which may affect the accuracy of the basic structure.

The basic principle of operation is referred to as the Coulter principle and described in said U.S. Pat. No. 2,656,508. According to this principle, the passage of a microscopic particle suspended in a conducting liquid through an aperture, having dimensions which approximate those of the particle, cuases a change in the resistance of the electrical path through the liquid effectively contained in the aperture, if the material of the particle and the liquid have different conductivities. Studies have shown that the magnitude of this change is proportional to the volume of the particle where the cross-sectional area of the particle is smaller than the cross-sectional area of the aperture and the particle is smaller in diameter than the axial length of the aperture. This volume is the volume of actual particulate matter, irrespective of the geometric configuration of the particle.

The detection of the passage of a liquid-suspended particle through an aperture is called scanning. Scanning apparatus as generally known and used at present in accordance with the Coulter principle comprise two vessels of electrically non-conductive material, the first vessel having a small aperture in one of the insulating walls and being immersed in a conducting liquid contained in a second vessel. The conducting liquid, in which the particles are suspended, is forced to flow under pressure between the vessels through the aperture. A pair of scanning electrodes is suspended in the liquid, one being in each vessel on opposite ends of the aperture. The only hydraulic or electric current path between the bodies of liquid in the respective vessels is through the aperture. One commercial version of a highly successful scanning apparatus or scanner is shown in U.S. Pat. No. 2,869,078. Other similar apparatus are shown in U.S. Pat. Nos. 2,656,508; 2,985,830; 3,015,775 and 3,122,431.

The first commercial apparatus utilizing the principles described in U.S. Pat. No. 2,656,508 is known as the "Coulter Counter" Model A. This structure basically comprises an electric power source having a high output series impedance which causes it to resemble a current source and a high input impedance, voltage sensitive signal detecting device. The power source and the detecting device are connected with the scanning electrodes in the manner shown in FIG. 7 of U.S. Pat. No. 2,656,508. The only difference between the commercial structure of the Model A and the circuit shown in the patent is that the battery illustrated in the patented circuit is replaced by an alternating current powered high d.c. voltage supply.

Under proper conditions, the apparatus mentioned above will generate electric pulses, the respective amplitudes of which are linear functions of the volumes of the respective particles passing through the aperture of the scanner, and it is therefore relatively simple to calibrate the structure. However, the prior structure is sensitive to changes in its environment, particularly when these changes cause variations in the conductivity of the liquid medium in which the particles are suspended.

The conductivity of the liquid medium is a function of the composition, temperature and concentration of the liquid. A change in conductivity will vitiate the calibration of the apparatus such that a given pulse amplitude will no longer represent a given particle size.

This sensitivity to the liquid conductivity requires that the instrument be recalibrated each time a new liquid is used, each time the concentration is changed and each time the temperature is changed.

The reason for this loss of calibration is easy to understand. The high input impedance signal detecting means is sensitive to the voltage appearing across the scanner electrodes. This voltage is a function of the resistance of the electric path through the aperture of the scanner, which in turn is dependent upon liquid conductivity. This voltage is also a function of the electric current flowing through the aperture, which in turn, is a function of the capacity of the power source to supply sufficient power, the size of the source series impedance and the conductivity of the liquid.

Stability of calibration and independence of liquid conductivity were first achieved by the circuit of the "Coulter Counter" Model B which is another commercial apparatus which utilizes the principles taught in U.S. Pat. No. 2,656,508 — and improves it according to the teachings of U.S. Pat. No. 3,259,842.

. The circuit of the Model B Coulter apparatus comprises a "constant" current source and a low input impedance pulse analyzer or signal detecting device the latter being in parallel connection with the scanner electrodes. The theory of operation upon which the improvement is based is that if a constant current is fed to the parallel circuit comprising the scanner electrodes and the low impedance input terminals of the analyzer, any change in the resistance measured across the scanner electrodes caused by the passage of a particle through the aperture of the scanner will cause changes in the currents of both of the parallel branches which are a function of the particle volume.

The Model B Coulter apparatus has enabled the achievement of remarkable results in particle analysis. Its current supply should be constructed to have a high output terminal impedance; yet, it must be well filtered to prevent the introduction of a.c. hum and noise into the analyzer circuits. Further, the input circuits of the pulse analyzer require complicated feedback networks to maintain a low input impedance and to control the gain in the amplifier stages.

SUMMARY OF THE INVENTION

This invention is directed to an apparatus for studying the physical properties of particles in a liquid suspension, the liquid suspension being separated into two bodies and an electrode being in each body. A partition is arranged between the bodies and has an aperture defining a path for enabling the passage of the suspension between the bodies. A power source is coupled with the suspension in said path for establishing an electric current through the suspension in said path, such that the passage of particles in the path will produce a train of electric signals, and an electric signal detecting circuit is connected in said apparatus. Circuit means couples the elements of the apparatus in such a manner that the d.c. current in the aperture path is made to vary inversely proportional to slow changes of resistivity of the aperture path with voltage remaining constant; yet, under particle signal frequency conditions, the aperture current remains constant and the changes in aperture resistance due to the presence of particles causes the generation of detectable voltage signals.

Accordingly, the primary object of this invention is to provide particle analyzer which can achieve the same results as the Model B by means of simpler and less expensive circuits which have flexible design parameters.

Another object of this invention is to provide an inexpensive particle analyzer whose calibration is independent of changes in conductivity of the aperture liquid.

Another object of the invention is to employ a d.c. short-circuiting device for enabling independence of conductivity changes in a particle analyzer.

These and other objects and advantages of the invention will be more clearly understood from a detailed description of preferred embodiments set forth below. The drawings are primarily diagrammatic and symbolic in nature in order to keep the description concise and intelligible, as those who are skilled in the art are familiar with many of the specific amplifier, detector and voltage source circuits which are suitable for constructing the combinations to be described.

BRIEF DESCRIPTION OF THE DRAWINGS

FIG. 1, labeled PRIOR ART, is a block diagram of the basic circuit of the Coulter Counter Model A;

FIG. 2, is a block diagram, simplified according to Thevenin's Theorem, of the basic circuit of FIG. 1, as it applies to signal frequencies;

FIG. 3, also labeled PRIOR ART, is a block diagram of the basic circuit of the Coulter Counter Model B;

FIG. 4, is a block diagram of the basic circuit of FIG. 3, simplified according to Thevenin's Theorem, as it applies to signal frequencies;

DESCRIPTION OF THE PREFERRED EMBODIMENTS

Figure 6:
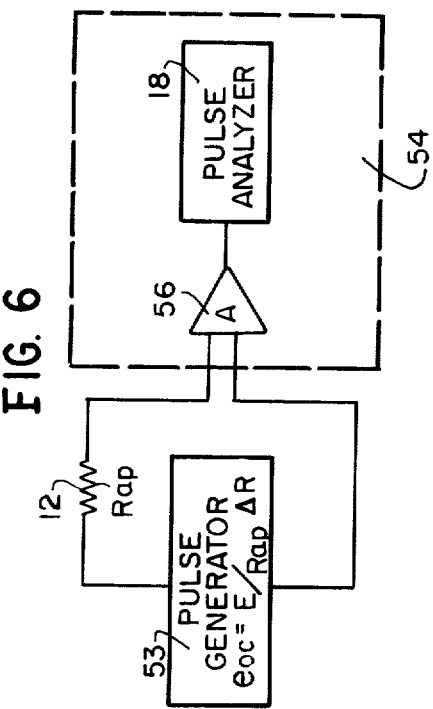
FIG. 6 is a block diagram of the basic circuit of FIG. 5, simplified according to Thevenin's Theorem, as it applies to signal frequencies.

In order to facilitate the understanding of the concept of this invention, reference is made to the principles of Coulter Counter Models A and B.

The basic circuitry of the Coulter Counter Model A, shown in FIG. 1, is of very simple design. Its operation now is well known and for many years was accepted as the only way of connecting the Coulter type of sensing means into a practical particle counter.

Referring to FIG. 1, a relatively high voltage power source 10 is connected to the parallel combination of a scanning apparatus 12, hereinafter called the aperture, and a voltage sensitive signal detecting device 14 by means of a pair of electrodes 12$a$ and 12$b$, which are described in detail in the aforementioned patents and need not be elucidated further herein. The signal detecting device 14 includes a high input impedance amplifier 16 and a pulse analyzer 18 connected to the output side of the amplifier 16. In an actual apparatus constructed in accordance with the U.S. Pat. No. 2,656,508, the power source 10 has a voltage of 300 volts. A high series impedance or resistance 20 by which the power source is coupled to the aperture is larger by several orders of magnitude than the impedance or resistance Rap between the electrodes 12$a$ and 12$b$ of the scanning apparatus. The changes in aperture resistance which normally are encountered have such a negligible effect upon the total series resistance load in the power source that the current Iap that flows in the aperture 12, which is the applied voltage divided by the total resistance, is for all practical purposes constant with regard to changes in aperture resistance. Controls can be incorporated which enable the selection of different values of the series resistance 20 to permit the use of different aperture sizes and electrolyte conductivities. The "constant current" is constant with the stipulation that the series resistance 20 is not changed. However, in practice, it is quite constant over the range of aperture resistances which might be expected under a given set of operating conditions. It will be appreciated that the power source 10 and the series impedance 20 define a current source 21.

When a particle passes through the aperture, it produces a change of aperture resistance $\Delta R$ which is proportional to the particle volume and the electrolyte resistivity, and is inversely proportional to the square of the cross sectional area of the aperture perpendicular to its axis in the most commonly encountered Coulter Counter. Since the current which flows through the aperture resistance is forced to be constant by the high series impedance 20, the voltage across the aperture raises by an amount $I_{ap}\Delta R$ for the duration of the particle passage. The d.c. component of the voltage drop across the aperture resistance is blocked by a capacitor 22, so only the signal voltage $I_{ap}\Delta R$ is applied to the high input impedance amplifier 16 of the voltage sensitive detecting device 14.

It may be well to point out that the capacitor 22 has two functions i.e. that of preventing the d.c. aperture current from flowing into the input of the amplifier 16, such that the aperture current is diminished by that amount, and of preventing the appreciable voltage drop across the aperture resistance, typically ten volts, from being applied to the input of the amplifier. The capacitor 22 accomplishes these ends by having practically infinite reactance at the excitation frequency, d.c. in this case, and practically zero reactance at signal frequencies.

Referring now to the equivalent circuit shown in FIG. 2, according to Thevenin's theorem, the current in any impedance connected to two terminals of a network, is the same as if the impedance was connected to a simple generator, such as a pulse generator 23 in FIG. 2, whose generated voltage is the open circuit voltage at the terminals in question and whose impedance is the impedance of the network looking back from the terminals, with all generators being replaced by impedances equal to the internal impedance of these generators. In this case, the simplification permitted by this theorem is of less import, since it is necessary only to measure the open circuit voltage $I_{ap}\Delta R$ developed by the aperture 12. However, it will become more significant in explaining the basic circuit of the Model B shown in FIG. 3, and finally the present invention shown in FIG. 5.

Although the circuit connections and the Thevenin equivalent circuit in FIGS. 3 and 4 are identical with those of the Model A as shown in FIGS. 1 and 2, the amplifier 36 for the Model B, as shown in FIGS. 3 and 4, has extremely low input impedance. In addition, the commercial Model B has an electronically regulated aperture current supply, making its power source 10 and the high series impedance 20 have effectively infinite voltage and impedance, respectively, and thus define a current source 31.

The current source 31 forces a current $I_{ap}$ through the scanning apparatus 12. None of the d.c. current can reach the low impedance amplifier 36 because of the blocking capacitor 22. As mentioned above, the current source may be electronically regulated, in which case as long as the setting of the regulator control is not changed, the current $I_{ap}$ is not affected by the aperture resistance. When the setting is changed, the magnitude of the current $I_{ap}$ changes to a new value and then remains functionally constant, except as explained in the aforementioned U.S. Pat. No. 3,259,842. For the present purposes, it may be considered constant.

The scanning apparatus or scanner 12, for the present to be thought of as consisting of a Coulter aperture, having a pair of electrodes 12a and 12b, is connected in series with the current source 31. A current sensitive signal detecting device 34, having the amplifier 36 which has a low input impedance at frequencies contained in the signal pulses, is connected to the electrodes 12a and 12b of the scanner 12. The output of the amplifier 36 is connected to the pulse analyzer 18. Although these elements appear to be in parallel, examination of which of them is the source and which is the load reveals that, when the power excitation is considered, the current source 31 is in series connection with the parallel combination of the scanner 12 and the detecting device 34. However, the signal itself arises in the scanner so that for the signal frequencies, it may be said that the scanner 12 is in series with the parallel combination of the current source 31 and the detecting device 34. Since the current source has for all practical purposes an infinite internal impedance, it may be neglected, leaving only the scanner and the detecting device in series for the signal components.

The Thevenin equivalent of FIG. 3 is shown in FIG. 4 and comprises the pulse generator 23 having the open circuit voltage $I_{ap}\Delta R$, with its internal impedance, and the aperture resistance $R_{ap}12$, so that the signal current that flows into the input terminals of the detector 34, which has for all practical purposes zero input impedance, is simply the open circuit voltage divided by the aperture resistance. As has been shown by many researchers, the change of the resistance $\Delta R$ is:

$$\Delta R = \frac{\rho \cdot v}{A_o 2},$$

and the resistance $R_{ap}$ of the aperture is $$R_{ap} = \frac{\rho \cdot l}{A_o}$$

by the definition of resistivity. Wherein $A_o$ is the cross sectional area of the aperture normal to its axis, 1 is its effective length, $\rho$ is the electrolyte resistivity, and $v$ is the volume of the particle. Therefore, the signal current $i_{sig}$ may be written:

$$i_{sig} = \frac{I_{ap} \frac{\rho \cdot v}{A_o 2}}{\frac{\rho \cdot l}{A_o}} \quad (1)$$

which reduces immediately to $$i_{sig} = \frac{I_{ap} \cdot v}{A_o l}$$

Since the resistivity term does not appear in this expression, the response of such a circuit does not depend upon it.

Figure 5:
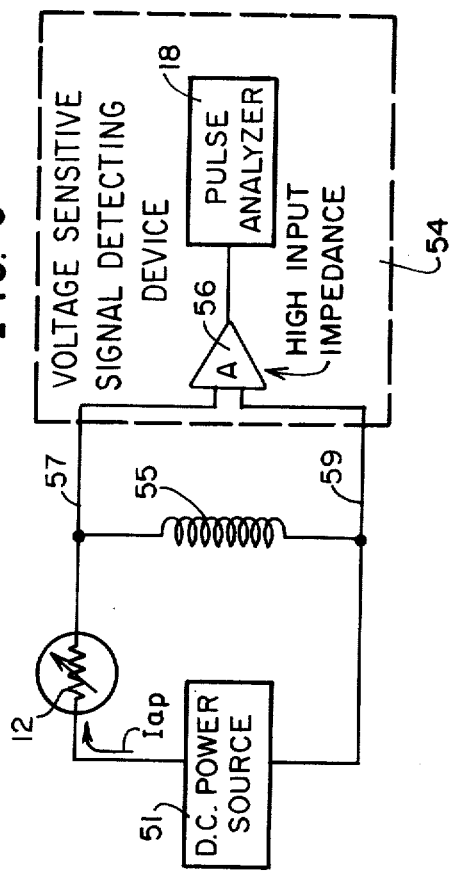
FIG. 5 is a block diagram of the basic circuit of the present invention.

In FIG. 5, the basic circuit of the present invention is shown. A low impedance, relatively low voltage supply of d.c. power 51 is connected in series with the aperture 12 and the parallel combination of a d.c. short-circuiting device 55 and a high input impedance amplifier 56. The d.c. short-circuiting device 55 is connected over leads 57 and 59 to the input of the high input impedance of the amplifier 56, which in combination with the pulse analyzer 18 that is connected to the output side of the amplifier 56 form a voltage sensitive signal detecting device 54. The d.c. short-circuiting device 55 has a very low d.c. resistance and a very high resistance or impedance at the frequencies of the trains of particle produced signal pulses transmitted from the scanning apparatus 12. Although the d.c. short-circuiting device 55 is illustrated in FIG. 5 as an inductance and most simply may be an inductance, it could be defined by a "black box" containing amplifiers and power sources or the like which displays the aforementioned impedance-frequency characteristics. The low resistance of the d.c. power source and the d.c. short-circuiting device cause the only current limiting resistance around the series loop of the apparatus to be that of the aperture 12, as symbolically emphasized in FIG. 5.

Considering the signal frequency situation, the source is the aperture 12 itself, but since it and the power source 51 are in series, the connection is the same as before. However, the impedance of the power source is so low as to be negligible, and the impedance of the d.c. short-circuiting device 55 is by design so large at signal frequencies that these elements may be omitted in drawing the Thevenin equivalent circuit shown in FIG. 6. If desired, the impedance of the d.c. short-circuiting device may be lumped into and considered part of the input impedance of the amplifier 56, lowering it somewhat, but not below several orders of magnitude greater than the aperture resistance 12. Having done these things, the Thevenin equivalent becomes quite simple, as shown in FIG. 6, which needs no further comment except to note that $$\frac{E}{R_{ap}}$$

is made deliberately a variable current $I_{ap}$, in contrast to the d.c. current $I_{ap}$ produced by the generator 23 in FIGS. 2 and 4.

With respect to the embodiment of FIG. 5, the following mathematical relationships now will be appreciated: the aperture current $I_{ap}$ is simply the source voltage E divided by the aperture resistance:

$$I_{ap} = \frac{E}{R_{ap}}. \quad (2)$$

By the previous explanation, the change of resistance due to the passage of a particle and the aperture resistance are respectively:

$$\Delta R = \frac{\rho v}{A_o^2} \quad (3)$$

and $$R_{ap} = \frac{\rho l}{A_o}. \quad (4)$$

Also, the open circuit voltage $e_{oc}$ developed by the change of resistance of the aperture is:

$$e_{oc} = I_{ap} \Delta R. \quad (5)$$

Since the impedance of the detecting amplifier 56 is many times higher than that of the aperture 12, there is no voltage divider action, and the entire open circuit voltage is impressed upon the amplifier.

Substituting the above values of $I_{ap}$, $\Delta R$, and $R_{ap}$ into equation 5:

$$e_{oc} = \frac{E}{R_{ap}} \Delta R = \frac{E}{\frac{\rho l}{A_o}} \frac{\rho v}{A_o^2}, \quad (6)$$

which simplifies immediately into $$e_{oc} = \frac{Ev}{A_o l}. \quad (7)$$

Thus we have an expression for the open circuit voltage fed into the detecting amplifier in which $\rho$, the resistivity of electrolyte is missing, again confirming that the response of the FIG. 5 apparatus is independent of the resistivity or conversely, the conductivity, of the electrolyte.

A more intuitive understanding may be had by considering that since the aperture resistance is all that limits the aperture current, and since the change of resistance is proportional to the aperture resistance, that is to say always the same percentage of it for a given size particle, if the aperture resistance is doubled due to a halving of the electrolyte conductivity, the resistance change due to a particle also will double, but the d.c. aperture current will drop to half of its former value. Twice the resistance change multiplied by half the excitation current will leave the signal unchanged.

The d.c. short-circuiting device 55 relieves the high-impedance amplifier of the necessity of passing the relatively large d.c. aperture current, which would otherwise saturate the amplifier 56, and permits the d.c. to flow, analogously with the way in which the blocking capacitor 22 of FIG. 3 prevents the low impedance amplifier 36 from bleeding away the aperture current and saturating in the process.

Figure 7:
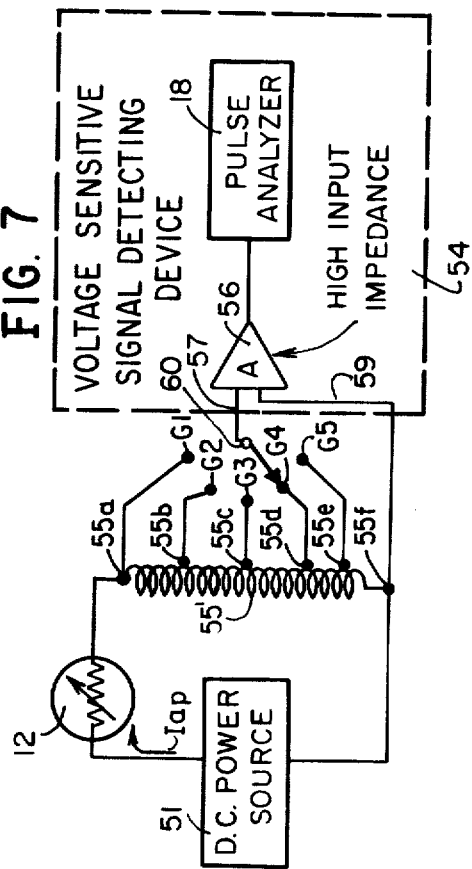
FIG. 7 is a diagram of an embodiment of the invention which incorporates the features of the circuit of FIG. 5 and additionally provides for changes in sensitivity by means of a tapped inductor.

The general arrangements in FIG. 7 are similar to those in FIG. 5, except for the fact that an inductor coil 55' with tappings 55a to 55f has been substituted for the simple inductor coil 55 in FIG. 5. The tapping points 55a to 55e are connected, respectively, to stator contacts $G_1$ to $G_5$ of a rotary switch 60 which can be operated by means of a control knob on the front panel of the apparatus. The rotor of the switch 60 is connected over the lead 57 to one input terminal of the amplifier 56 of the signal detecting device 54. The other lead 59 connects the coil terminal 55f with the second input terminal of the amplifier 56.

The use of the tapped inductor 55' controls the size of the signal pulses that are fed to the amplifier 56 and provides an economical means for adjusting the gain of the apparatus. The circuitry of the detecting device 54 may be simplified, because there is no necessity of providing it with a gain control or designing it to operate over a wide range of signal levels. Instead, the detecting device may be constructed to have optimum performance at one narrow range of signals. Further, the changes in the gain of the apparatus caused by the operation of switch 60 can be accurately determined, since they are a function of the inductor turns ratio.

From the foregoing, it now should be apparent that the present invention, as described with respect to the specific embodiments of FIGS. 5 and 7 but not limited thereto, is formed from elements, subcombinations of elements, and combinations thereof which, taken as a whole, are not present in the prior art particle analyzers shown in FIGS. 1 and 3. Not only, as above described, are the embodied parallel-series relationships different from the prior art under d.c. as well as signal frequency conditions, but generically speaking, there is developed a controlled current condition not present in the prior art embodiments of FIGS. 1 and 3.

More specifically, the present invention provides for a deliberately variable aperture current in response to conductivity changes in the particle suspension; whereas, in response to the rapid changes in the impedance of the aperture path due to the passage therethrough of particles, the aperture current remains substantially constant, forcing the derived voltage signals to be proportionate to the presence of the particles and independent of electrolyte resistivity and its slow changes. Stated differently, the d.c. aperture current is inversely proportional to the aperture impedance and voltage remains constant; yet, the open circuit voltage is the product of a constant aperture current and the changes in the aperture path resistance.

As stated with respect to the Model A embodiment shown in FIG. 1, it is not constructed for operating in a mode of independence from changes in electrolyte resistivity. Although the Model B embodiment, shown in FIG. 3, operates in an independence of resistivity mode, such independence is not achieved by providing for any changes in the aperture current, in fact, the aperture current remains constant under both d.c. and signal conditions. Accordingly, although the ultimate result of independence of resistivity is common to the present invention and the Model B embodiment, this result is accomplished by two different combinations of elements interacting in two different manners.

Although only the basic concept directed to specific structure and coactions of the present invention have been set forth herein, embellishments thereof are considered to be encompassed and lie within the spirit and scope of the invention as claimed.

What I desire to be secured by United States Letters Patent is:

1. An apparatus for studying the physical properties of particles in a liquid suspension, the liquid suspension being separated into two bodies, electrode means in each body, an insulating partition between the bodies having an aperture defining a path therein for enabling the passage of the suspension between the bodies, the passage of a single particle through the path resulting in a displacement of the suspension in the path, electric detecting means electrically coupled with the suspension in said path, means for establishing an electric current to pass through the suspension in said path, the electrical properties of the particles and of the suspension being sufficiently different such that the passage of particles in said path will produce a train of electric voltage signals for detection by said detecting means, the improvement comprising: circuit means which couples said path, detecting means, and electric current establishing means of the apparatus in such a manner that the current in said path is made to vary inversely proportional to slow changes of resistivity of the aperture path with voltage remaining constant; yet, under particle signal frequency conditions, the aperture current remains constant and the changes in aperture resistance due to the presence of particles causes the generation of detectable voltage signals.

2. An apparatus according to claim 1 in which said circuit means includes a d.c. short-circuiting device having a very low d.c. impedance and a very high impedance at the frequencies of the particle produced electric signals.

3. An apparatus according to claim 2 in which said short-circuiting device has terminal leads coupled, respectively, to the electrode means in one of said bodies and said current establishing means, and has output means coupled to said detecting means.

4. An apparatus according to claim 2 in which said short-circuiting device and said detecting means are coupled in a parallel combination in said apparatus, and the current establishing means is coupled in series with said path and said parallel combination for all together defining a series loop.

5. An apparatus according to claim 4 in which said current establishing means has a significantly lower impedance than said path and said detecting means has a significantly higher input impedance than said path and, in combination with the low d.c. impedance of said short-circuiting device, defines the only significant current limiting resistance of the series loop as the impedance of said path.

6. An apparatus according to claim 1 in which said circuit means is series coupled to said current establishing means, and said detecting means has an input impedance significantly higher than the impedance of said path.

7. An apparatus according to claim 6 in which said circuit means has terminal leads coupled, respectively, to the electrode means in one of said bodies and said current establishing means, and has output means coupled to said detecting means.

8. An apparatus according to claim 7 in which said circuit means primarily comprises passive electrical component means.

9. An apparatus according to claim 8 in which said circuit means comprises an inductance means.

10. An apparatus according to claim 8 in which said circuit means consists of an inductor connected in parallel with said detecting means.

11. An apparatus for studying the physical properties of particles in a liquid suspension, the liquid suspension being separated into two bodies, an electrode in each body, and an insulating partition between the bodies having an aperture defining a path therein for enabling the passage of the suspension between the bodies, said apparatus comprising:
   A. means producing a flow of the suspension through said path so that the passage therethrough of a single particle will result in a displacement of the suspension in the path,
   B. electric signal detecting means electrically coupled with the suspension in said path,
   C. means for establishing an electric current to pass through the suspension in said path, the electrical properties of the particles and of the suspension being sufficiently different such that the passage of particles in said path will produce a train of electric signals, for detection by said detecting means, the improvement comprising
      a. said means establishing an electric current comprising a power source having first and second electrical leads and an output impedance which is significantly lower than the impedance of said path, the first lead being connected to one of the electrodes and providing a steady-state d.c. current to said path;
      b. a d.c. short-circuiting device having a very low d.c. impedance and a very high impedance at frequencies of the particle produced electric signals, said short-circuiting device having a pair of input terminals and output terminals means,
         i. one input terminal being connected to the other of the electrodes,
         ii. the second input terminal being connected to the second lead of the power source;
      c. said electrical signal detecting means having input leads connected with said output terminal means of said short-circuiting device, placing these two elements electrically in parallel in said apparatus, said detecting means having a significantly higher input impedance than the impedance of said path;

d. a series loop formed by said power source, said path, and said parallel combination of the d.c. short-circuiting device and the high input impedance detecting means;

e. the low resistance of the power source and the low d.c. resistance of the d.c. short-circuiting device in combination defining the resistance of the aperture as the only direct current limiting resistance in said series loop;

f. whereby each time that a particle passes through said path, the electric current in the path remains constant and there will be produced an electrical signal whose amplitude is a function of the size of the particle, and whose duration is equal to the time that the particle is in the path; and g. the combination of
   i. the impedances of the power source, the path and the amplifier being on an ascending line in magnitudes, with
   ii. the circuit arrangement of said loop series of the power source, the path and said parallel relation of the short-circuiting device and the amplifier, providing that a slow change proportionate the resistivity of the liquid suspension causes an inverse proportionate change of the current in said path, such that the apparatus attains an independence from such slow resistivity changes.

12. The apparatus as set forth in claim 11, wherein the d.c. short-circuiting device comprises an inductor having a low d.c. resistance and a high impedance at frequencies of the particle produced electric signals.

13. The apparatus as set forth in claim 1, wherein the d.c. short-circuiting device comprises a tapped inductor.

14. The apparatus as set forth in claim 11, wherein the power source is a d.c. source.

15. The apparatus as set forth in claim 11, wherein the power source is of low voltage.

16. The apparatus as set forth in claim 11, wherein the electric signal detecting device is a voltage sensitive device.

17. A method for the compensation of the temperature-dependency of the conductivity of an electrically conductive liquid during pulse amplitude measurement of particles suspended in the liquid by means of a conductivity cell, especially during the determination of the average volume of blood particles, comprising the steps of supplying the conductivity cell over its liquid-temperature dependent low-frequency range by a voltage source and over its useful frequency range for pulse amplitude measurement by a current source, and using at least one frequency filter for separating the low-frequency range from the useful frequency range.

18. An apparatus for compensating the temperature-dependency of the conductivity of an electrically conductive liquid during pulse amplitude measurement of particles suspended in the liquid by means of a conductivity cell comprising means for compensating the temperature-dependency of the electrically conductive liquid, said compensating means embodying a constant direct-current voltage source and at least one frequency filter, the conductivity cell being electrically coupled with the constant direct-current voltage source and said frequency filter.

19. The apparatus as defined in claim 18, wherein said frequency filter is an inductance, said inductance being dimensioned such that in the useful frequency range wL is much greater than the resistance of the conductivity cell and for low-frequency changes wL is much smaller than the resistance of the conductivity cell, said inductance, the constant direct-current voltage source and the conductivity cell being electrically connected in series, and output leads for pulse amplitude measurements electrically connected with the conductivity cell.

20. The apparatus as defined in claim 19, wherein the inductance comprises a coil.

* * * * *

UNITED STATES PATENT AND TRADEMARK OFFICE
CERTIFICATE OF CORRECTION

PATENT NO. : 3,993,948
DATED : November 23, 1976
INVENTOR(S) : Sheldon L. Epstein It is certified that error appears in the above-identified patent and that said Letters Patent are hereby corrected as shown below:

Column 4, line 36, change "Rap" to -- $R_{ap}$ --; line 40, change "Iap" to -- $I_{ap}$ --. Column 6, lines 16 and 32, change "$A_o2$" to -- $A_o^2$ --; line 26, change "1" to -- $\ell$ --. Column 7, lines 37 and 58, change "$A_o2$" to -- $A_o^2$ --; line 58, after "$\frac{E}{\rho\ell \ A_o}$", add the multiplication symbol -- • --; line 64, change "$\frac{Ev}{A_o 1}$" to -- $\frac{Ev}{A_o \ell}$ --. Column 11, lines 23-28, the entire phrase "providing...changes." should be printed commencing at the left margin and not indented; lines 23 and 24, delete "proportionate" and insert therefore -- in --.

Signed and Sealed this

Twenty-fourth Day of May 1977

[SEAL]

Attest:

RUTH C. MASON
*Attesting Officer*

C. MARSHALL DANN
*Commissioner of Patents and Trademarks*